United States Patent [19]

Wesley et al.

[11] Patent Number: 5,202,425
[45] Date of Patent: Apr. 13, 1993

[54] **OLIGODEOXYNUCLEOTIDE PROBES FOR *CAMPYLOBACTER FETUS* AND *CAMPYLOBACTER HYOINTESTINALIS***

[75] Inventors: Irene V. Wesley; Ronald D. Wesley, both of Ames, Iowa

[73] Assignee: The United States of America as represented by the Secretary of Agriculture, Washington, D.C.

[21] Appl. No.: 603,503

[22] Filed: Oct. 26, 1990

[51] Int. Cl.$^5$ .................. C07H 15/12; C12Q 1/68; C12Q 1/02
[52] U.S. Cl. ........................... 536/24.3; 435/6; 435/29
[58] Field of Search .............. 536/26, 27, 28, 29

[56] References Cited

PUBLICATIONS

Louis M. Thompson III et al., "Phylogenetic Study of the Genus Campylobacter," Int. J. System. Bacteriol. 38(2): 190–200 (Apr. 1988).

Paul P. Lau et al., "Phylogenetic Diversity and Position of the Genus Campylobacter," System. Appl. Microbiol. 9: 231–238 (1987).

Paul J. Romaniuk et al., "Identification of Campylobacter Species by Southern Hybridization of Genomic DNA Using an Oligonucleotide Probe for 16S rRNA Genes," FEMS Microbiol. Lett. 43: 331–335 (1987).

C. J. Gebhart et al., "Species-Specific Cloned DNA Probes for the Identification of *Campylobacter hyointestinalis*," J. Clin. Microbiol. 27(12): 2717–2723 (Dec. 1989).

E. J. Schrawder et al., "Detection of Campylobacter by Colony Hybridization With Colorimetric Oligonucleotide Probes," Abstr. 113, Clin. Chem. 34(6): 1176 (1988).

P. Moreau et al., "Campylobacter Species Identification Based on Polymorphism of DNA Encoding rRNA," J. Clin. Microbiol. 27(7): 1514–1517 (Jul. 1989).

I. V. Wesley et al., "Development of Nucleic Acid Probes for *Campylobacter fetus* and *Campylobacter hyointestinalis*," Abstract for 1989 Annual meeting of American Assoc. of Vet. Lab. Diagnost., Oct. 28–31, 1989, Las Vegas, NV.

Irene V. Wesley, "Nucleic Acid Probes for *Campylobacter fetus* and *Campylobacter hyointestinalis* Based on 16S Ribosomal RNA (16S rRNA) Analysis," Abstr. Cl 302, 19th Annual Meeting, UCLA Symposia on Molecular & Cellular Biology, Feb. 3–Mar. 11, 1990 (J. Cell. Biochem.).

*Primary Examiner*—Amelia Burgess Yarbrough
*Assistant Examiner*—Stephanie W. Zitomer
*Attorney, Agent, or Firm*—M. Howard Silverstein; John D. Fado; Curtis P. Ribando

[57] ABSTRACT

Single-stranded DNA probes complementary to a hypervariable region of Campylobacter 16S rRNA are useful in distinguishing species of this pathogen from one another. The probes find practical application in diagnosing human and animal diseases caused by this organism from clinical samples, such as fecal material. They are also useful in differentiating Campylobacter species based on RFLP analyses.

5 Claims, No Drawings

OLIGODEOXYNUCLEOTIDE PROBES FOR *CAMPYLOBACTER FETUS* AND *CAMPYLOBACTER HYOINTESTINALIS*

BACKGROUND OF THE INVENTION

1. Field of the Invention

This invention relates to nucleic acid probes useful for differentiating two closely related species of Campylobacter, *C. Fetus*, and *C. hyointestinalis*.

The genus Campylobacter is composed of spirally curved gram negative pathogens with characteristic darting motility but few metabolic characteristics useful in species differentiation. The genus encompasses pathogens of human and veterinary importance, including *Campylobacter fetus* and *Campylobacter hyointestinalis*. A vibroid bacterium, *Vibrio fetus*, has been recognized as the etiological agent of bovine and ovine infertility and abortion. This pathogen has been isolated from the placenta of aborting sheep, stomach contents of aborted fetuses and from blood, and also intestinal contents of infected ewes and cattle. The abortifacient species *C. fetus* was subsequently subdivided into two subspecies which are differentiated according to their tolerance to 5% glycine. *C. fetus* subsp fetus is transmitted orally, induces abortion in sheep, and rarely produces septicemia in humans; whereas *C. fetus* subsp venerealis is exclusively a venereal pathogen of animals. *C. fetus* subsp fetus replicates at 42° C. and grows in the presence of glycine, whereas the subspecies venerealis replicates at 37° C. and is intolerant of glycine [Smibert, "Genus Campylobacter Seabld and Veron 1963, 907$^{AL}$," pp. 111-118 In N. R. Krieg and J. G. Holt (ed., Bergey's Manual of Systematic Bacteriology, Vol. I, Williams and Wilkins, Baltimore]. *C. fetus* shares a 16-30% DNA homology with *C. hyointestinalis* with which it is most closely related. *C. hyointestinalis* produces $H_2S$ in triple sugar iron in contrast to *C. fetus*. The two species may also be distinguished via fatty acid profiles. *C. hyointestinalis* was first described in association with swine proliferative ileitis and has also been reported in health cattle and as an enteric pathogen of humans.

2. Description of the Prior Art

Nucleic acid hybridization using total genomic DNA has been used in the taxonomy [Fennel et al., J. Clin Microbiol 24:146-148 (1986); Steele et al., J. Clin Microbiol 22:71-74 (1985); Totten et al., J. Infect. Dis. 151:131-139 (1985); Von Sulffen, FEMS Microbiol Lett. 42:129-133 (1987); Chevrier et al., J. Clin. Microbiol. 27:321-326 (1989] and in the diagnosis [Tomkins et al., Diagn. Microbiol. Infect. Dis. 4:71S-78S (1988) of Campylobacter. Nucleic acid probes have been developed for the genus Campylobacter [Freier et al., Clin. Chem. 34:1176 (1988)]; *C. jejuni* [Picken et al., Mol. Cel Probes 1:245-259 (1987); Korolik et al., J. Gen Microbiol. 134:521-529 (1988)]; *C. hyointestinalis* [Gebhart, J. Clin. Microbiol. 27: 2717-2723 (1989)]; and the *C. coli—C. jejuni—C. laridis* complex [Shrawder et al., Clin. Chem. 34:1176 (1988)].

Although the nucleotide sequences of ribosomal RNAs (rRNA) have been conserved through evolution, mutations have occurred as species diverge [Gray et al., Nucl. Acids Res. 12:5837-5852 (1984); Lane et al., Proc. Natl. Acad. Sci. U.S.A. 82:6955-6959 (1985); Woese et al., Microbiol. Rev. 47:621-629 (1983)]. Many of these changes exist in hypervariable regions. Oligonucleotides complementary to these regions have been synthesized which disciminate very closely related species. The 5S and 16S rRNA sequences of Campylobacter species have been examined for the purpose of studying the phylogeny and diversity of the genus, and partial sequences have been reported [Lau et al., Syst. Appl. Microbiol. 9:231-238 (1987); Romaniuk et al., FEMS Microbiol. Lett. 43:331-335 (1987); Paster et al., Intl. J. Syst. Bacteriol. 38:56-62 (1988); Tompson et al., Intl. J. Syst. Bacteriol. 38:190-200 (1988)]. Though deoxyligonucleotide probes specific for 16S rRNA have been reported for the genus Campylobacter [Moureau et al., J. Clin. Microbiol. 27:1514-1517 (1989); Rashtchian et al., Current Microbiol. 14:311-317 (1987); Romaniuk et al., 1987, supra; Wesley, J. Cell. Biochem. Suppl. 14C:182 (1990)] hypervariable regions between *C. fetus* and *C. hyointestinalis* have not been previously identified.

SUMMARY OF THE INVENTION

We have nearly fully sequenced the 16S rRNA in *C. fetus* and in *C. hyointestinalis* and have identified a hypervariable region which allows the rRNA of these two species to be distinguished from one another. Based on this information, we have constructed oligodeoxynucleotide probes which are designed to specifically hybridize with DNA or rRNA target sequences associated with the hypervariable region of each of these Campylobacter species. The probes are particularly useful for accelerating the clinical identification of these pathogens from bacterial cultures.

In accordance with this discovery, it is an object of the invention to provide a rapid and effective alternative to conventional biochemical and serological methods of identifying campylobacters.

It is also an object of the invention to provide highly specific and selective oligonucleotide probes useful for clinical diagnosis of diseases induced by *C. fetus* and *C. hyointestinalis*.

It is a specific object of the invention to provide an assay for detecting bacterial agents responsible for abortion in livestock and proliferative ileitis in swine.

Other objects and advantages of this invention will become readily apparent from the ensuing description.

GLOSSARY

For purposes of this invention, the following standard abbreviations and terms used herein have been defined below. Also included are a listing of biological materials and reagents mentioned in the specification.

| ABBREVIATIONS | |
|---|---|
| ATCC = | American Type Culture Collection |
| At$^{32}$P = | $^{32}$P-labelled adenosine triphosphate |
| bp = | base pairs |
| DNA = | deoxyribonucleic acid |
| NADC = | National Animal Disease Center, Ames, Iowa |
| RFLP = | restriction fragment length polymorphism |
| RNA = | ribonucleic acid |
| rRNA = | ribosomal ribonucleic acid |
| ss-rRNA = | single-stranded ribosomal ribonucleic acid |
| SDS = | sodium dodecyl sulfate |
| VPI = | Virginia Polytechnic Institute |

TERMS

DNA or RNA sequence: a linear series of nucleotides connected one to the other by phosphodiester bonds between the 3' and 5' carbons of adjacent pentoses.

hybridization: the pairing together or annealing of complementary single-stranded regions of nucleic acids to form double-stranded molecules.

hypervariable region: region within highly conserved 16S rRNA to which nucleotide changes occur most frequently.

nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C") and thymine ("T"). The four RNA bases are A, G, C and uracil ("U").

oligonucleotide: a linear series of 2-100 deoxyribonucleotides or ribonucleotides connected one to the other by phosphodiester bonds between the 3' and 5' carbons of adjacent pentoses.

oligonucleotide probe: a single-stranded piece of DNA or RNA that can be used to detect, by hybridization or complementary base-pairing, a target nucleic acid sequence which is homologous or complementary.

sequence: two or more DNA or RNA nucleotides in a given order.

stringency: refers to the conditions under which hybridization takes place. At high stringency only exact matches of DNA and RNA will hybridize stably. Under low stringency, nonhomologous sequences may hybridize.

DETAILED DESCRIPTION OF THE INVENTION

In preparation for developing oligonucleotide probes of the invention, we determined nearly the full nucleotide sequences of the 16S rRNA molecule of *C. fetus* subsp fetus (ATCC 27274), *C. fetus* subsp venerealis (ATCC 19438) and *C. hyointestinalis* (NADC 2006 and ATCC 35217). Upon comparison of these sequences, regions of the *C. fetus* species 16S rRNA molecule that differed from analogous regions of the *C. hyointestinalis* 16S rRNA were identified. One such region, hereafter referred to as the hypervariable region, was selected. This region is represented by the ss-rRNA sequences of the aforementioned deposit strains shown in Table III and in the appended Sequence Listing as SEQ ID NOS. 1-4. In Table III, nucleotide mismatches amongst the strains are underlined.

A strategy for constructing a probe within the scope of the invention is initiated by predetermining the probe's length. It is envisioned that probes useful herein would range in size from about 10 to 50 bases, with the preferred size being about 15 to 30 bases. A sequence of the predetermined length, occurring within the 16S rRNA and including at least one of the base mismatches in the hypervariable region is then selected. In order to avoid the need for highly stringent conditions during hybridization, the selected sequence preferably includes at least two base mismatches. Optimally, the probe would include all eight of the recognized mismatches in the hypervariable region. The nucleotide sequence complementary to the selected rRNA sequence is thereafter determined, and the oligodeoxyribonucleotide probe is synthesized as the inverse of the complementary sequence. In this way, the probe is in correct orientation for binding to native DNA or rRNA in samples to be assayed.

Given below in the Sequence Listing as SEQ ID NO. 5 is the base sequence corresponding to the inverse of the complement of the *C. fetus* subsp venerealis rRNA or *C. hyointestinalis* extending 50 bases upstream and 40 bases downstream from the hypervariable region. In SEQ ID NO. 5, the IUPAC code N, representing any nucleotide, has been used whenever a mismatch between the sequences originating from *C. fetus* or *C. hyointestinalis* occurred at a given position or when the nucleotide at a given position was undetermined for both species The sequences of probes encompassed by the invention can be ascertained directly from SEQ ID NO. 5 in conjunction with SEQ ID NOS. 1-4. Examples of such probes are represented as SEQ ID NOS. 6-8, discussed further below.

Under appropriately stringent conditions, a probe of the invention will bind only to DNA or rRNA of the Campylobacter species it was designed to detect. This specificity makes these probes useful for the unequivocal detection of *C. fetus* or *C. hyointestinalis* in complex samples such as fecal material.

The derivation of probes as outlines above has several advantages over cloned genomic DNA probes. When the target of the probe is rRNA, increased sensitivity is obtained because the rRNA is present in up to 10,000 copies per cell as opposed to only 1-10 gene copies per cell. Also short oligonucleotide probes can be used with substantially reduce the hybridization time. This results in a highly sensitive and specific test that can be completed in 5 days or less.

These probes are useful in a variety of hybridization formats. The approach which is most readily applied to a laboratory setting is the colony blot, in which the probe is reacted with bacterial colonies. The slot blot technique uses either bacterial colonies which are subsequently lysed, or else chromosomal DNA which may be harvested with commercially available DNA extraction kits. The Southern blot hybridization protocol would be useful for deducing taxonomic relationships.

In addition, the probes of the invention can be used to differentiate between Campylobacter species based on RFLP analysis. DNA isolated from bacteria are digested with restriction endonucleases, the fragments are separated by electrophoresis through an agarose gel, transferred to a solid support, and hybridized with the oligonucleotide probe. When probed in this way, the Campylobacter species can be differentiated based on the positions of the DNA bands that hybridize with the probe. This application is epidemiologically useful for following the transmission of a particular organism.

To enable detection, the probes may be bound to a radioactive, enzymatic, or organic label by any conventional procedure in the art. For instance, by leaving the 5'—OH end nonphosphorylated during construction, the probes are readily end-labelled using T4 polynucleotide kinase and $\gamma$ AT$^{32}$P as described in Example 2.

The following examples are intended only to further illustrate the invention and are not intended to limit the scope of the invention which is defined by the claims.

EXAMPLE 1

Selection of Bacterial Strains and Growth Conditions

Bacterial strains were obtained from the American Type Culture collection (ATCC), National Animal Disease Center (NADC), and Virginia Polytechnic Institute (VPI) collections. The following ATCC reference strains of Campylobacter were evaluated: *C. cina-*

*edi* ATCC 35683, *C. coli* ATCC 33559, *C. concisus* ATCC 33237, *C. cryaerophila* ATCC 43158, *C. faecalis* ATCC 33709, *C. fenneliae* ATCC 35684, *C. fetus* subsp fetus ATCC 27374, *C. fetus* subsp venerealis ATCC 19438, *C. hyointesitinalis* ATCC 35217, *C. laridis* ATCC 35221, *C. jejuni* ATCC 33560, *C. mucosalis* ATCC 43264, *C. nitrofigilis* ATCC 33309, *C. sputorum subsp. bubulus* ATCC 33562, and *C. sputorum* subsp sputorum ATCC 35980. The *C. upsaliensis* strain (D1914) was obtained from the Center for Disease Control, Atlanta, Ga.

Field isolates of *C. fetus* (n=53) and *C. hyointestinalis* (n=55) examined in this study are shown in Tables I and II, respectively. Isolates were characterized as *C. fetus* based on characteristic morphology, motility, site of isolation from the host, growth at 42° C., and failure to generate $H_2S$. Isolates of *C. hyointestinalis* were confirmed as such by $H_2S$ production, tolerance of glycine, sensitivity to nalidixic acid and cephalothin and fatty acid profiles. In addition, serologic cross-reactivity with *C. fetus* was evaluated in a microtiter agglutination assay [Firehammer et al., Amer. J. Vet. Res. 47:1415-1418 (1986)]. Two strains of *C. jejuni* (NADC 1829 and NADC 1990) were also included as negative controls.

Bacteria were grown on brain heart infusion agar (BHIA) with 10% defibrinated bovine blood and incubated microaerophilically (10% $CO_2$ and 90% air; 72 hr at 37° C.).

EXAMPLE 2

16S Ribosomal RNA Sequence Analysis

RNA was isolated and partially purified as described by Paster et al. [1988, supra]. Complete 16S ribosomal RNA sequences were determined for *C. hyointestinalis* (ATCC 35217 and NADC 2006), *C. fetus* subsp fetus (ATCC 27374 and VPI H641), and for *C. fetus* subsp venerealis (ATCC 19438). These sequences were compared with published partial sequences of *Campylobacter concisus, C. fetus* subsp fetus, *C. jejuni, C. coli, C. laridis, C. sputorum, C. pylori,* a campylobacter of ferrets, *Bacterioides gracilis, B. ureolyticus, Wolinella recta, W. curva, W. succinognes, Escherichia coli, Citrobacter freundii, Proteus vulgaris,* and the unpublished sequence of *Flexispira rappini*. The computer program of Paster et al. [1988, supra] was used for data entry, editing, sequence alignment, secondary structure comparison, homology matrix generation, and dendrogram construction for 16S rRNA data. Nucleic acid sequences which were selected for probes were identified by alignment of 16S rRNA sequence data, identification of common bases and selection of regions where mismatches occurred. Commercially prepared oligonucleotides (Synthecell, Gaithersburg, Md.) were end-labelled with $^{32}P$ $\gamma$ ATP by the T4 polynucleotide kinase reaction as described [Richardson, Proc. Nucl. Acid Res. 2:815 (1971)].

A total of 1413 bases were sequenced for 16S ribosomal RNA of *C. fetus* and *C. hyointestinalis*. Alignment of nucleic acids indicated that a single base mismatch (position 811) differentiated *C. fetus* subsp fetus from the subspecies venerealis. In contrast, a 28 oligonucleotide difference distinguished *C. fetus* from *C. hyointestinalis*. Based on sequence data, it was demonstrated that *C. fetus* subsp fetus shared a 99.8% to 100% sequence homology with the subspecies venerealis and a 98% sequence identity with *C. hyointestinalis*.

A region of 8 mismatches (from position 1017 to 1046) was identified. The rRNA sequence data for this hypervariable region for each of *C. fetus* subsp venerealis (ATCC 19438), *C. fetus* subsp fetus (ATCC 27374), *C. hyointestinalis* (NADC 2006), and *C. hyointestinalis* (ATCC 35217) are given in Table III and also in the Sequence Listing as SEQ ID NOS. 1-4, respectively. Two *C. fetus*-specific probes, a 17-oligodeoxynucleotide probe (5'CTC-AAC-TTT-CTA-GCA-AG 3'; SEQ ID NO. 6) and a 29-oligodeoxynucleotide probe (5'CTC-AAC-TTT-CTA-GCA-AGC-TAG-CAC-TCT-CT-3'; SEQ ID NO. 7) were synthesized from the hypervariable region. These probes do not encompass the single base mismatch which exists between *C. fetus* subsp fetus and *C. fetus* subsp venerealis. Also a 29-oligodeoxynucleotide probe (5'-CAC-TAA-TTT-CIT-GTA-AAC-AAG-CAC-TAT-CT-3'; SEQ ID NO. 8) specific for *C. hyointestinalis* was synthesized.

EXAMPLE 3

To determine the specificity for the appropriate microbe, the three probes prepared in Example 2 were tested in a colony blot hybridization format against reference strains of 16 Campylobacter species and subspecies as follows.

Colony Blot Hybridization

A nylon membrane ("GeneScreen," NEN Research Products, Dupont deNemours and Company, Inc., Boston, Miss.) was gently pressed over bacterial colonies (3-4 days old) grown on BHIA containing 10% defibrinated bovine blood. After a minimum of 1 hr the membrane was denatured (0.5M NaOH, 1.5M NaCl), neutralized (1M tris, 3M NaCl, pH 5.5) and UV crosslinked to covalently bind the DNA to the membrane filters. Hybridization was carried out at (37° C. for 18 hr) in 6X SSC (SSC is 0.15M NaCl, 0.015M Na citrate, pH 7.0), 5X Denhardt's solution (0.1% Ficoll, 0.1% polyvinylpyrrolidone, 0.1% bovine serum albumin), 0.5% SDS, and 100 $\mu$g/ml of sonicated denatured calf thymus DNA. The hybridization solution contained $10^6$ cpm of the appropriate end-labelled $^{32}P$ oligonucleotide probe. After incubation, filters were washed once briefly in 2X SSC-0.1% SDS at room temperature, followed by two stringency washes. For *C. fetus* (17-mer) stringency washes were completed in saline sodium citrate (1X SSC, 37° C., 1 hr) whereas the 29-mer specific for *C. fetus* required higher stringency conditions (47° C. in 0.1X SSC). For *C. hyointestinalis* the stringency washes were performed in 6X SSC (50° C., for 1 hr). Dried filters were exposed to Kodak "X-Omat" film with two intensifying screens ($-80$° C., 1 day).

As shown in Table IV, the two *C. fetus* specific oligonucleotides hybridized only with the reference strains of *C. fetus* subsp fetus (ATCC 19438) and *C. fetus* subsp venerealis (ATCC 27374). No reaction was seen with any of the other reference strains of Campylobacter, including the phylogenetically closely related *C. hyointestinalis*. The *C. hyointestinalis* specific probe hybridized only with the colony blots of the *C. hyointestinalis* reference strain (ATCC 35217). No cross reaction was observed with the closely related *C. fetus* strains (ATCC 19438 and ATCC 27374).

EXAMPLE 4

Specificity of each of the *C. fetus* probes was evaluated further in a slot blot format against genomic DNA of field strains as follows.

Slot Blot Hybridization

For slot blot hybridization, high molecular weight genomic DNA was extracted from bacterial cells as described by Wesley et al. [Amer. J. Vet. Res. 50:807–813 (1989)]. A series of preliminary experiments was carried out to determine the appropriate hybridization and washing conditions to maximize the signal to background ratio. Typically, 2 μg/well of Campylobacter genomic DNA was applied to a "GeneScreen" nylon membrane (NEN Research Products, Dupont deNemours and Company, Inc., Boston, Mass.) in a slot-blot apparatus (Biorad, Richmond, Calif.). The DNA was denatured, neutralized, and UV crosslinked as described above for colony blot hybridization. Prehybridization was carried out for 3 hr at 37° C. in 6X SSC. 5X Denhardt's solution, 0.5% SDS, and 100 μg/ml of sonicated denatured calf-thymus DNA. Hybridization and stringency washes were conducted as described above for colony blot hybridization. Radiolabelled probes which hybridized to target nucleic acids were visualized by autoradiography with Kodak "X-Omat" film and DuPont intensifying screens (=80° C. 1 day).

The C. fetus-specific probes hybridized equally well with genomic DNA of 49 of 53 field strains of C. fetus of bovine, human, or ovine origin. In a typical hybridization, the C. fetus-specific oligonucleotides hybridized equally well with isolates of the subspecies fetus (ATCC 27374, NADC 1992) and venerealis (ATCC 19438, NADC isolates 1986, 1987, 1988, 1989, 1991). No hybridization occurred with genomic DNA isolated from either C. hyointestinalis (ATCC 35217) or from C. jejuni (NADC 1990). The field strains which did not hybridize were identified as follows. No hybridization occurred with two bovine isolates (NADC 5-DLF and NADC 27-J46), which, after Hha I digestion, exhibited a restriction enzyme pattern atypical of C. fetus and were subsequently identified as C. sputorum bubulus (data not shown). A bovine isolate (NADC 2460), which failed to react with the C. fetus probe did, however, hybridize with the oligonucleotide for C. hyointestinalis and was subsequently identified biochemically as such. An ovine isolate (NADC 2462) did not react with the C. fetus probe and was reidentified as a C. jejuni strain, which was inadvertently included in these studies.

The C. hyointestinalis-specific probe was appraised using genomic DNA of 55 field isolates of C. hyointestinalis. A typical hybridization result indicated that this probe reacted with the prototype reference strain and 14 of 18 field strains, but not with C. fetus subsp fetus (ATCC 27374), subsp venerealis (ATCC 19438), or C. jejuni. Three porcine field isolates (1585-G5, 1585-G7, and 1585-G8), which were initially identified as C. hyointestinalis based on anatomical site of recovery and weak $H_2S$ production, did not react with the probe under stringency conditions (6X SSC, 50° C.), used in these studies. However, relaxing the stringency conditions (4X SSC, 45° C.), resulted in a weak signal. Restriction enzyme analysis has shown these to be clones of a single strain. Isolate NADC 1705, which did not react with the C. hyointestinalis probe, was subsequently identified as C. fetus. In further assays, other isolates which did not hybridize with the C. hyointestinalis probe were identified as follows. NADC isolates 1589.2, 1705, and 2029 failed to hybridize with the oligonucleotide for C. hyointestinalis, but did react with the C. fetus specific probe and were subsequently verified as such biochemically. The human strains NADC isolate 1997, which was initially described as an atypical Campylobacter-like organism (CLO), and isolate NADC 2020 failed to react with probes for either C. hyointestinalis or for C. fetus. Isolate NADC 2020 was subsequently identified biochemically as C. jejuni; isolate NADC 1997 was not identified further.

EXAMPLE 5

The three probes described in Example 2 were evaluated in Southern blot hybridization of genomic DNA extracted from field isolates and cleaved with the restriction endonuclease Bgl II. This assay was performed as follows.

Southern Blot Hybridization

Genomic DNA was digested with Bgl II and restriction fragments size separated in 0.6% agarose gels (60V, 18 hr), blotted onto "GeneScreen" nylon membranes using the method of Southern (1975), and UV crosslinked as described by Church et al. [Proc. Natl. Acad. Sci. U.S.A. 81:1991–1995 (1984)]. To detect the presence of 16S rRNA genes, nylon filters were prehybridized (3 hr) and then hybridized (18 hr, 37° C.) with $5 \times 10^6$ cpm of the appropriate $^{32}p$ end-labelled oligonucleotide probe as described above. Membranes were washed once in 2X SSC, 0.1% SDS at room temperature. For C. fetus (17-mer) two stringency washes were completed in saline sodium citrate (1X SSC, 37° C., 1 hr)whereas the 29-mer required stringency washes at 47° C., in 0.1X SSC. Stringency washes for the C. hyointestinalis oligonucleotide were performed in 4X SSC (45° C., 1 hr). Dried filters were exposed to Kodak "X-Omat" film with two intensifying screens (−80° C., 2–7 days).

Nucleic acid sequences homologous with the oligonucleotide probes specific for the C. fetus 16S rRNA genes were localized within no more than three restriction fragments (9.0, 7.7, 7.0 kb). Hybridization occurred with two common restriction fragments (9.0 7.7) whereas reactivity with a third smaller restriction fragment (7.0 kb) was occasionally noted. Southern blot hybridization of C. hyointestinalis strains digested with the endonuclease Bgl II and probed with the C. hyointestinalis specific oligonucleotide indicated that sequences encoding 16S rRNA genes were localized within no fewer than three restriction fragments: 10.1, 8.2, and 7.2 kb.

It is understood that the foregoing detailed description is given merely by way of illustration and that modification and variations may be made therein without departing from the spirit and scope of the invention.

TABLE I

| | Strains of Campylobacter fetus | |
|---|---|---|
| Source | No. of Strains | NADC strain identification |
| Human | 9 | 2591, 2592, 2954, 2595, 2596, 2597, 2598, 2599, 2600 |
| Bovine | 42 | 5-DLF$^a$, 6-RCM, 7-9C30, 9-DLF, 10-71, 11-46, 13-G26, 14-K287, 15-K6, 18-F91, 19-L53, 21-A11, 21-H23, 21-G36, 21-G83, 22, 25-G28, 27-J46$^a$, 44–77, 1289, 1826, 1827, 1828, 1830, 1831, 1832, 1833, 1986, 1987, 1988, |

TABLE I-continued

| Strains of Campylobacter fetus | | |
|---|---|---|
| Source | No. of Strains | NADC strain identification |
| | | 1989, 1991, 1992, 2456, 2457, 2458, 2459, 2460[b], 2461, 2646, 2705, 2716 |
| Ovine | 2 | 2462[c], 2642 |

[a] Isolates 5-DLF and 27-J46 failed to hybridize with the C. fetus probe and were subsequently reidentified as C. sputorum subsp bubulus.
[b] Isolate 2460 failed to hybridize with the C. fetus probe but did react with the probe for C. hyointestinalis.
[c] Isolate reidentified as C. jejuni.

TABLE II

| Strains of C. Hyointestinalis | | |
|---|---|---|
| Source | No. of Strains | NADC strain identification |
| Porcine | 21 | 1585-G4, 1585-G5, 1585-G6, 1585-G7, 1585-G8, 1585-G9, 1705[a], 1819, 1821, 1825, 1916, 1917, 1919, 1920, 2000, 2001, 2002, 2027, 2028, 2034, 2641 |
| Human | 21 | 1996, 1997[b], 1998, 2006, 2007, 2008, 2009, 2018, 2019, 2020[b], 2021, 2022, 2023, 2024, 2025, 2026, 2037, 2261, 2262, 2263, 2264 |
| Bovine | 13 | 1492, 1493, 1587, 1589.2[a], 1592, 1593, 2029[a], 2031, 2032, 2033, 2035, 2036, 2038 |

[a] NADC isolates 1589.2, 1705, and 2029 hybridized with the probe specific for C. fetus and failed to react with the C. hyointestinalis-specific oligomer.
[b] NADC isolates 1997, 2020 failed to react with the probe for either C. fetus or C. hyointestinalis. Isolate NADC 2020 was identified as C. jejuni; isolate NADC 1997 was not identified further.

TABLE III

| 16S rRNA from Campylobacter Species | | | |
|---|---|---|---|
| C. fetus subsp venerealis (ATCC 19438) | AGA$\underline{G}$AGUGCU | AG$\underline{C}$UUGCUAG | AAA$\underline{GU}$ $\underline{UG}$ $\underline{A}$GA |
| C. fetus subsp fetus (ATCC 27374) | AGA$\underline{G}$AGUGCU | NG$\underline{C}$UUGCUAG | AAA$\underline{GU}$ $\underline{UG}$ $\underline{A}$GA |
| C. hyointestinalis (NADC 2006) | AGA$\underline{U}$NGUNCU | NG$\underline{U}$UUNCNAG | AAA$\underline{U}$UNG$\underline{U}$GA |
| C. hyointesinalis (ATCC 35217) | AGA$\underline{U}$NGUNCU | UG$\underline{U}$UU$\underline{AC}$AAG | AAA$\underline{UU}$ $\underline{AG}$ $\underline{U}$GA |
| POSITION | 5' 1017 | | 1046 3' |

TABLE IV

| | Colony Blot Hybridization | |
|---|---|---|
| Species | C. fetus (17-mer, 29-mer) | C. hyointestinalis (29-mer) |
| C. cineadi ATCC 35683 | — | — |
| C. coli ATCC 33559 | — | — |
| C. concisus ATCC 33237 | — | — |
| C. cryaerophila ATCC 43158 | — | — |
| C. faecalis ATCC 33709 | — | — |
| C. fenneliae ATCC 35684 | — | — |
| C. fetus subsp fetus ATCC 27374 | + | — |
| C. fetus subsp venerealis ATCC 19438 | + | — |
| C. hyointestinalis ATCC 35217 | — | + |
| C. jejuni ATCC 33560 | — | — |
| C. laridis ATCC 35221 | — | — |
| C. mucosalis ATCC 43264 | — | — |
| C. nitrofigilis ATCC 33309 | — | — |
| C. sputorum subsp bubulus ATCC 33562 | — | — |
| C. sputorum subsp sputorum ATCC 35980 | — | — |
| C. upsaliensis D1914 | — | — |

We claim:

1. A labelled, single-stranded DNA probe having a length of about 15-50 bases, wherein the base sequence of said probe consists essentially of a sequence encompassed by SEQ ID NO. 5 and including at least one of the bases N in a region of SEQ ID NO. 5 extending from position 51 through position 80, wherein said bases N are selected to be uniquely complementary to either C. fetus or C. hyointestinalis.

2. A single-stranded DNA probe as described in claim 1, wherein said length is 17-35 bases and wherein the probe includes at least four bases N in said region all of which are uniquely complementary to either C. fetus or c. hyointestinalis.

3. A single-stranded DNA probe as described in claim 1, wherein said probe is the 17-base sequence of SEQ ID NO. 6.

4. A single-stranded DNA probe as described in claim 1, wherein said probe is the 29-base sequence of SEQ ID NO. 7.

5. A single-stranded DNA probe as described in claim 1, wherein said probe is the 29-base sequence of SEQ ID NO. 8.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: rRNA ( i i i ) HYPOTHETICAL: NO ( i v ) ANTI-SENSE: NO ( v i ) ORIGINAL SOURCE:
        ( A ) ORGANISM: Campylobacter fetus
        ( B ) STRAIN: fetus
        ( C ) INDIVIDUAL ISOLATE: ATCC 27374

(ix) FEATURE:
    (A) NAME/KEY: miscdifference
    (B) LOCATION: replace(51..80, "")
    (D) OTHER INFORMATION: /note="bases 51-80 constitute a
        hypervariable region corresponding to bases
        1017-1046 of the 16S rRNA"

(xi) SEQUENCE DESCRIPTION: SEQ ID NO:1:

| | | | | | | |
|---|---|---|---|---|---|---|
| ACGCGAAGAA | CCUUACCUNG | GCUUNAUAUC | CAACUNAUCU | CUUAGAGAUN | AGAGAGUGCU | 60 |
| NGCUUGCUAG | AAAGUUGAGA | CAGGUGCUGC | ACGGCUGUCG | UCAGCUCGUG | UCGUGAGAUG | 120 |

(2) INFORMATION FOR SEQ ID NO:2:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Campylobacter fetus
        (B) STRAIN: venerealis
        (C) INDIVIDUAL ISOLATE: ATCC 19438

(ix) FEATURE:
        (A) NAME/KEY: miscdifference
        (B) LOCATION: replace(51..80, "")
        (D) OTHER INFORMATION: /note="bases 51-80 constitute a
            hypervariable region corresponding to bases
            1017-1046 of the 16S rRNA"

(xi) SEQUENCE DESCRIPTION: SEQ ID NO:2:

| | | | | | | |
|---|---|---|---|---|---|---|
| ACGCGAAGAA | CCUUACCUGG | GCUUGAUAUC | CAACUNAUCU | CUUAGAGAUA | AGAGAGUGCU | 60 |
| AGCUUGCUAG | AAAGUUGAGA | CAGGUGCUGC | NCGGCUGUCG | UCAGCUCGUG | UCGUGAGAUG | 120 |

(2) INFORMATION FOR SEQ ID NO:3:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: rRNA (vi) ORIGINAL SOURCE:
        (A) ORGANISM: Campylobacter hyointestinalis
        (C) INDIVIDUAL ISOLATE: NADC 2006

(ix) FEATURE:
        (A) NAME/KEY: miscdifference
        (B) LOCATION: replace(51..80, "")
        (D) OTHER INFORMATION: /note="bases 51-80 constitute a
            hypervariable region corresponding to bases
            1017-1046 of the 16S rRNA"

(xi) SEQUENCE DESCRIPTION: SEQ ID NO:3:

| | | | | | | |
|---|---|---|---|---|---|---|
| ACGCGAAGAA | CCUUACCUNG | GNUUNAUAUC | CUNAUNACAU | CUUAGAGAUN | AGAUNGUNCU | 60 |
| NGUUUNCNAG | AAAUUNGUGA | CAGGUGCUGC | ACGGCUGUCG | UCAGCUCGUG | UCGUGAGAUG | 120 |

(2) INFORMATION FOR SEQ ID NO:4:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (  i  i  ) MOLECULE TYPE: rRNA (  v  i  ) ORIGINAL SOURCE:
        ( A ) ORGANISM: Campylobacter hyointestinalis
        ( C ) INDIVIDUAL ISOLATE: ATCC 35217

(  i  x  ) FEATURE:
        ( A ) NAME/KEY: miscdifference
        ( B ) LOCATION: replace(51..80, "")
        ( D ) OTHER INFORMATION: /note="bases 51-80 constitute a
              hypervariable region corresponding to bases
              1017-1046 of the 16S rRNA "

(  x  i  ) SEQUENCE DESCRIPTION: SEQ ID NO:4:

```
ACNNGNAGAA  CCUUACCUNG  GCUUNAUAUC  CUNAUNACAU  CUUAGAGAUA  AGAUNGUNCU      60

UGUUUACAAG  AAAUUAGUGA  NAGGUGCUGC  NCGGCUGUCG  UCAGCUCGUG  UCGUGAGAUG     120
```

( 2 ) INFORMATION FOR SEQ ID NO:5:

(  i  ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear (  i  i  ) MOLECULE TYPE: cDNA to rRNA (  v  i  ) ORIGINAL SOURCE:
        ( A ) ORGANISM: Campylobacter (  i  x  ) FEATURE:
        ( A ) NAME/KEY: miscdifference
        ( B ) LOCATION: replace(41..70, "")
        ( D ) OTHER INFORMATION: /note="bases 41-70 are
            complementary to bases 51-80, resp. in SEQ ID NOS.
            1-4; bases 43, 45, 47, 53, 55, 58, 60, and 67 are (  x  i  ) SEQUENCE DESCRIPTION: SEQ ID NO:5:

```
CATCTCACGA  CACGAGCTGA  CGACAGCCGN  GGAGCACCTN  TCNCNANTTT  CTNGNAANCN      60

AGNACNNTCT  NATCTCTAAG  ANNTNANNNG  GATATNAANC  CNAGGTAAGG  TTCTNCNNGT     120
```

( 2 ) INFORMATION FOR SEQ ID NO:6:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i  i  ) MOLECULE TYPE: cDNA to rRNA (  i  x  ) FEATURE:
        ( A ) NAME/KEY: miscfeature
        ( B ) LOCATION: 1..17
        ( D ) OTHER INFORMATION: /product="probe"
            / note="corresponds to bases 42-58 of SEQ ID NO 5"

(  x  i  ) SEQUENCE DESCRIPTION: SEQ ID NO:6:

```
CTCAACTTTC  TAGCAAG                                                         17
```

( 2 ) INFORMATION FOR SEQ ID NO:7:

(  i  ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i  i  ) MOLECULE TYPE: cDNA to rRNA (  i  x  ) FEATURE:
        ( A ) NAME/KEY: miscfeature
        ( B ) LOCATION: 1..29

( D ) OTHER INFORMATION: /product="probe"
/ note="corresponds to bases 42-70 of SEQ ID NO.
5"

( x i ) SEQUENCE DESCRIPTION: SEQ ID NO:7:

CTCAACTTTC TAGCAAGCTA GCACTCTCT 29

( 2 ) INFORMATION FOR SEQ ID NO:8:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: cDNA to rRNA ( i x ) FEATURE:
( A ) NAME/KEY: miscfeature
( B ) LOCATION: 1..29
( D ) OTHER INFORMATION: /product="probe"
/ note="corresponds to bases 42-70 of SEQ ID NO.
5"

( x i ) SEQUENCE DESCRIPTION: SEQ ID NO:8:

CACTAATTTC TTGTAAACAA GCACTATCT 29